United States Patent [19]

Kitamura et al.

[11] Patent Number: 5,492,023
[45] Date of Patent: Feb. 20, 1996

[54] APPARATUS FOR AUTOMATICALLY DETERMINING RATE OF PLASTICIZER ABSORPTION OF RESIN POWDER

[75] Inventors: Hajime Kitamura, Ichihara; Masaru Takeuchi; Hideo Yoshikoshi, both of Hasaki; Mikio Kitai, Mito; Takashi Chino, Iruma; Yuji Nogami, Kawaguchi; Hajime Yashiro, Sagara; Keisuke Kato, Kawasaki, all of Japan

[73] Assignee: Shin-Etsu Chemical Co., Ltd., Japan

[21] Appl. No.: 171,738

[22] Filed: Dec. 22, 1993

[30] Foreign Application Priority Data

Jan. 4, 1993 [JP] Japan .................. 5-000096

[51] Int. Cl.⁶ ...................... G01N 5/02
[52] U.S. Cl. ...................... 73/866; 73/74
[58] Field of Search ............ 73/866, 74, 76; 265/44; 428/219, 402

[56] References Cited

U.S. PATENT DOCUMENTS

| | | | |
|---|---|---|---|
| 1,989,003 | 1/1935 | Dunagan | 265/44 |
| 2,679,159 | 5/1954 | Messer | 73/74 |
| 4,108,602 | 8/1978 | Hanson et al. | 73/866 |
| 4,271,698 | 6/1981 | Wingrave | 73/74 |
| 4,501,870 | 2/1985 | Kidoh et al. | 428/402 |
| 4,829,839 | 5/1989 | Fisher et al. | 73/866 |
| 4,837,776 | 6/1989 | Poll | 73/866 |
| 5,076,107 | 12/1991 | Timmermans et al. | 73/866 |
| 5,349,876 | 9/1994 | Le Gigan | 73/866 |
| 5,368,918 | 11/1994 | Harada et al. | 428/219 |

*Primary Examiner*—Richard Chilcot
*Assistant Examiner*—George M. Dombroske
*Attorney, Agent, or Firm*—Parkhurst Wendel & Rossi

[57] ABSTRACT

An apparatus for automatically determining the rate of plasticizer absorption of a powdery resin sample such as a vinyl chloride resin sample. The apparatus for automatically determining the rate of plasticizer absorption of a powdery resin sample is one in which the rate of plasticizer absorption is determined by treating, in a centrifugal separator 10, a powdery resin contained in an inspection container 2 together with an excess of a plasticizer, to remove from the powdery resin sample the excess plasticizer, and determining the amount of the plasticizer absorbed by and remaining in the powdery resin. The apparatus according to the present invention includes an electronic balance 3 for weighing out the powdery resin which is connected to an arithmetic circuit 61; an injection means 5 for injecting the plasticizer into the powdery resin; a disposal chute 6 for recovering the inspection container 2 already used in the weight-determination; and a suction device 7 for aspirating the plasticizer separated by and remaining in the centrifugal separator 10. The apparatus further includes a robot 4 for transferring the powdery resin contained in the inspection container 2 to the electronic balance 3, the plasticizer-injection means 5, the centrifugal separator 10 or the disposal chute 6; and a driving unit 15 for moving an aspiration port 9 of the suction device 7 up and down within the centrifugal separator 10.

5 Claims, 5 Drawing Sheets

APPARATUS FOR AUTOMATICALLY DETERMINING RATE OF PLASTICIZER ABSORPTION OF RESIN POWDER

BACKGROUND OF THE INVENTION

The present invention relates to an apparatus for automatically determining the rate of plasticizer absorption of a powdery resin such as vinyl chloride resins, ABS resins and MBS resins.

When preparing resin powder or forwarding the powdery product from a manufacturing plant, the product is in general subjected to quality inspection for various predetermined physical and/or chemical properties. The results thus obtained are sent back to the manufacturing plant for the improvement of production processes or they are used in the denoration of the quality thereof in order to afford convenience to the destination or the consignee.

In case of, for instance, vinyl chloride resin powder, one of the items for the quality inspection thereof is to inspect the powdery resin for the rate of plasticizer absorption. The term "the rate of plasticizer absorption of a powdery resin" herein means the amount of a plasticizer absorbed by a predetermined amount of resin powder. The rate of plasticizer absorption can in general be determined by weighing out a powdery resin sample, adding an excess &mount of a plasticizer to the weighed powdery resin sample, separating the excess plasticizer from the mixture after the powdery resin sample sufficiently absorbs the plasticizer and again weighing the powdery resin sample to determine the rate of plasticizer absorption of the sample on the basis of the weight gain. The rate of plasticizer absorption of a powdery resin can thus be determined, but there has not yet been developed any apparatus for automatically determining the rate of plasticizer absorption of a powdery resin sample.

Conventionally, the determination of the rate of plasticizer absorption has been carried out manually and accordingly, it requires much labor and time to carry out operations such as the operation for precisely weighing out a powdery resin sample and that for precisely weighing out a plasticizer absorbed. The manner of carrying out these operations slightly varies depending on operators and this is reflected in the measured values. In particular, it takes much labor and time to recover and/or abandon the plasticizer obtained during the separation of the excess plasticizer from a powdery resin sample.

SUMMARY OF THE INVENTION

It is an object of the present invention to provide an apparatus for automatically determining the rate of plasticizer absorption of a powdery resin sample which can provide reproducible measured values of the rate of plasticizer absorption of a powdery resin sample without requiring any manual operations which may adversely affect the measured values.

According to the present invention, the foregoing object can effectively be accomplished by providing an apparatus for automatically determining the rate of plasticizer absorption of a powdery resin in which the rate of plasticizer absorption is determined by treating, with a centrifugal separator, a powdery resin contained in an inspection container together with an excess of a plasticizer to remove the excess plasticizer from the powdery resin sample and determining the amount of the plasticizer remaining in the powdery resin, wherein the apparatus comprises an electronic balance for weighing out the powdery resin which is connected to an arithmetic circuit: an injection means for injecting the plasticizer into the powdery resin: a disposal chute for recovering the used inspection container; a suction device for aspirating the excess plasticizer separated by and remaining in the centrifugal separator; a robot for transferring the powdery resin contained in the inspection container to the electronic balance, the plasticizer-injection means, the centrifugal separator or the disposal chute; and a reciprocating-drive unit for moving an aspiration port of the suction device up and down within the centrifugal separator. The arithmetic circuit calculates the rate of plasticizer absorption of the powdery resin on the basis of the weight of the powdery resin after the centrifugation determined by the electronic balance and the weight of the powdery resin prior to the absorption of the plasticizer likewise determined by the electronic balance.

In a preferred embodiment of the present invention, the centrifugal separator is provided with a plurality of high speed-rotatable bottomed envelopes for accommodating the inspection container having a through hole on the bottom. Thus the plasticizer remaining in the envelopes can be removed by inserting the aspiration port of the suction device into the envelopes after picking out the inspection container from the envelope and then aspirating it through the aspiration port.

the foregoing preferred embodiment of the present invention, the apparatus further comprises a means for feeding, in order, the plurality of envelopes into the position at which the aspiration port moves up and down.

The means for feeding, in order, the envelopes also serves as a motor for rotating the envelopes at a high speed. In this case, the motor is rotated at a low speed under the control of a drive-control means, then the motor rotating at a low speed is stopped at an instance when a sensor arranged at a position corresponding to that of the aspiration port detects the presence of the envelope rotatable at a high speed and the aspiration port is inserted into the envelope by operating the reciprocation-drive unit after the robot picks out the inspection container.

DETAILED EXPLANATION OF THE INVENTION

Figure 1:
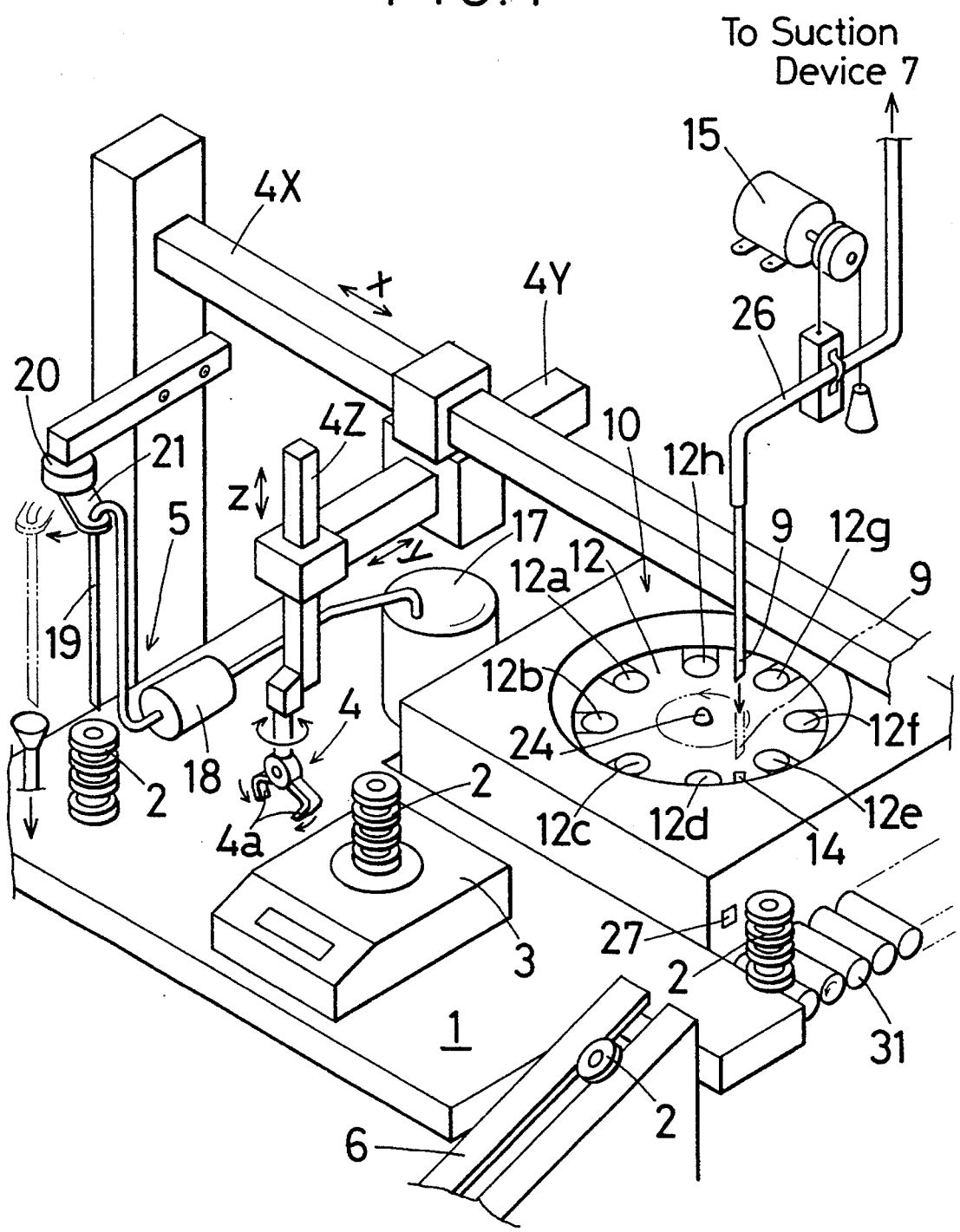
FIG. 1 is a perspective view showing an embodiment of the apparatus for automatically determining the rate of plasticizer absorption of a powdery resin according to the present invention.

The apparatus for automatically determining the rate of plasticizer absorption of a powdery resin according to the present invention will hereunder be described in more detail with reference to the accompanying drawings.

The apparatus according to the present invention is an apparatus for automatically determining the rate of plasticizer absorption of a powdery resin in which the rate of plasticizer absorption is determined by treating, with a centrifugal separator 10, a powdery resin contained in an inspection container 2 together with an excess of a plasticizer to remove the excess plasticizer and determining the amount of the plasticizer remaining in the powdery resin. The apparatus comprises an electronic balance 3 for weighing out the powdery resin which is connected to an arithmetic circuit 61 (see FIG. 3); an injection means 5 for injecting the plasticizer into the powdery resin; a disposal chute 6 for recovering the used inspection container 2; and a suction device 7 for aspirating the excess plasticizer separated by and remaining in the centrifugal separator 10. The apparatus further comprises a robot 4 for transferring the powdery resin contained in the inspection container 2 to the electronic balance 3, the plasticizer-injection means 5, the centrifugal separator 10 or the disposal chute 6; and a reciprocating-drive unit 15 for moving an aspiration port 9 of the suction device 7 up and down within the centrifugal separator 10. In the apparatus, the calculation of the rate of plasticizer absorption of the powdery resin sample is performed by the arithmetic circuit 61 on the basis of the weight of the powdery resin after the centrifugation determined by the electronic balance 3 and the weight of the powdery resin prior to the absorption of the plasticizer likewise determined by an electronic balance.

Figure 2:
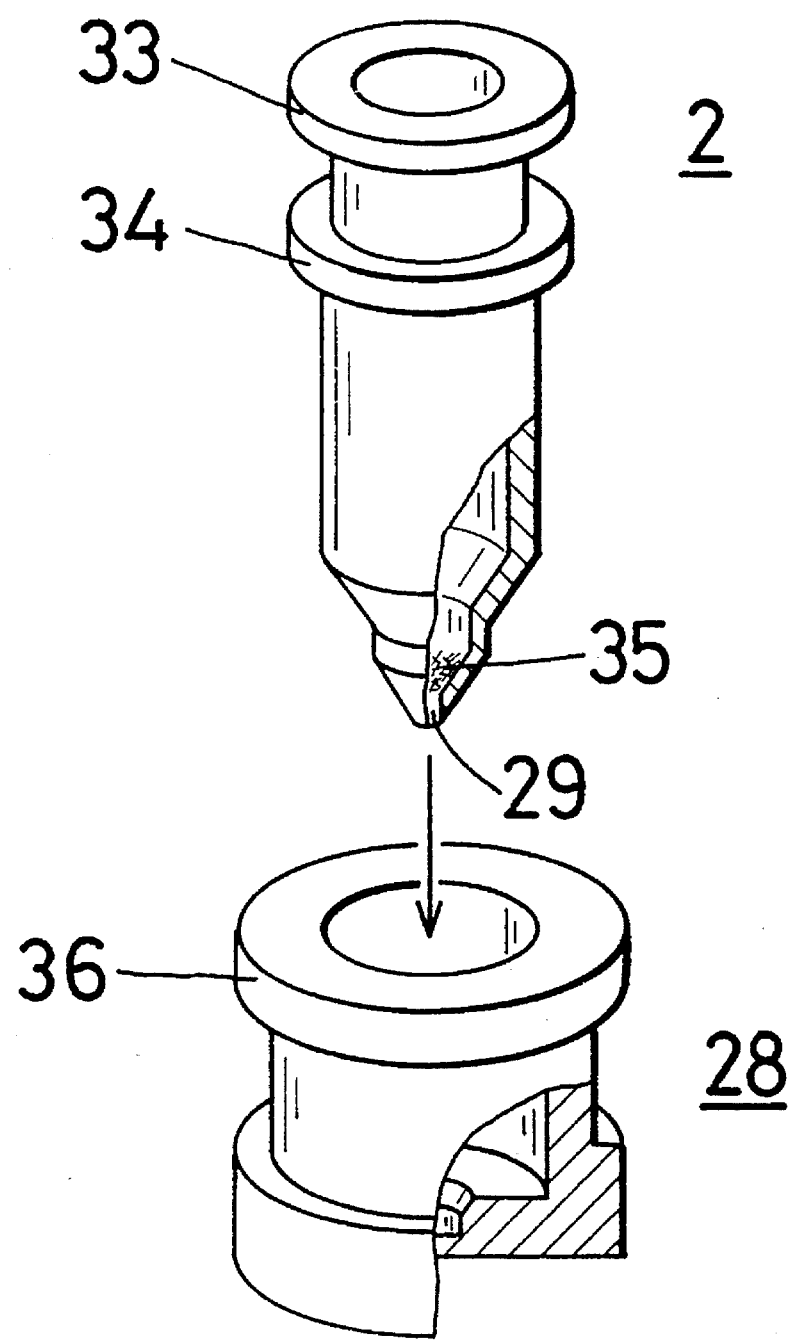
FIG. 2 is a cross sectional view showing a part of an inspection container and a carrier container used in the apparatus for automatically determining the rate of plasticizer absorption of a powdery resin according to the present invention.

The centrifugal separator 10 is provided with a plurality of high speed-rotatable bottomed envelopes 12a, 12b, 12c, . . . for accommodating the inspection container 2 having a through hole 29 on the bottom (see FIG. 2). Thus the plasticizer remaining in the plurality of envelopes 12a, 12b, 12c, . . . can be removed by inserting the aspiration port 9 of the suction device 7 into the envelopes after picking out the inspection container 2 and then aspirating it through the aspiration port 9. The apparatus preferably comprises a means for feeding, in order, the plurality of envelopes 12a, 12b, 12c, . . . into the position at which the aspiration port 9 undergoes its reciprocating motion. More specifically, the means for feeding, in order, the envelopes also serves as a motor 13 for rotating the envelopes 12a, 12b, 12c, . . . at a high speed (see FIG. 3). In this case, the motor 13 is rotated at a low speed under the control of a drive-control means 62, then the motor 13 rotating at a low speed is stopped at an instance when a sensor 14 arranged at a position corresponding to that of the aspiration port 9 detects the presence of the envelopes rotatable at a high speed and the aspiration port 9 is inserted into the envelope by operating the reciprocation-drive unit 15 after the robot 4 picks out the inspection container 2 therefrom.

The apparatus for automatically determining the rate of plasticizer absorption of a powdery resin can suitably be applied to, for instance, a powdery vinyl chloride resin.

According to the apparatus for automatically determining the rate of plasticizer absorption of a powdery resin, the calculation of the rate of plasticizer absorption of the powdery resin sample is performed by the arithmetic circuit 61 on the basis of the weight of the powdery resin after the centrifugation determined by the electronic balance 3 and the weight of the powdery resin prior to the absorption of the plasticizer likewise determined by an electronic balance. The procedures for the measurement of the rate of plasticizer absorption can automatically be performed and even after the measurement, the plasticizer remaining in the centrifugal separator 10 can likewise be automatically aspirated by the suction device 7. Therefore, after completion of a series of the procedures for the inspection of a powdery sample, the next determination procedures can immediately be initiated.

Some embodiments of the apparatus according to the present invention will hereunder be explained in detail with reference to the accompanying drawings, but the present invention is by no means limited to these specific embodiments.

FIG. 1 is a perspective view showing an embodiment of the apparatus for automatically determining the rate of plasticizer absorption of a powdery resin according to the present invention.

As seen from FIG. 1, an electronic balance 3 and a plasticizer-injecting means 5 are mounted and arranged on a table 1 of the apparatus. The plasticizer-injecting means 5 comprises a pump 18 and a plasticizer-storing tank 17 connected to the pump 18 through a tube and a delivery tube 19 of the pump 18 is suspended from a vibrating piece 21 which is fitted to a vibrational actuator 20. The plasticizer-storing tank 17 is filled with dioctyl phthalate (DOP) as a plasticizer used. The centrifugal separator 10 is positioned in the proximity to the table 1 of the apparatus.

The centrifugal separator 10 comprises a high speed motor 13 (see FIG. 3) and a rotating panel 12 firmly fitted to a rotation axis 24 connected to the motor 13 and eight bottomed envelopes 12a, 12b, 12c, 12d, 12e, 12f, 12g and 12h rotatable at a high speed are axially supported by the rotating panel 12. The aspiration port 9, which is connected to the suction device 7 through a tube 26, is arranged at a position above the centrifugal separator 10. The tube 26 is fitted to the reciprocating motor 15 in the middle of the tube 26 so that the aspiration port 9 can move up and down by the rotation of the motor 15. The aspiration port is designed such that, when any one of the envelopes 12a, 12b, 12c, 12d, 12e, 12f, 12g and 12h exists at a position immediately below the aspiration port 9, the aspiration port can descend down to the position near the bottom of the corresponding envelope. The centrifugal separator is provided with a proximity sensor 14 for detecting or confirming if the specified envelope is present at the position immediately below the aspiration port 9 or not. In addition, the centrifugal separator 10 may further comprise a cooling fan (not shown) in order to prevent any change in the rate of plasticizer absorption due to heat generated through the rotation of the centrifugal separator 10.

A roller conveyor 31 for conveying the inspection container 2 containing the powdery resin sample is fitted to the side of the table 1. The other end of the roller conveyor 31 is connected to an electronic balance 60 (see FIG. 3) which is omitted in FIG. 1. The electronic balance 60 is provided for determining the weight of the inspection container 2 containing the powdery resin sample prior to the inspection and the inspection container 2 is thus transferred from the electronic balance 60 to the table 1 after the determination of the weight thereof. A sensor 27 is arranged on the side face of the centrifugal separator 10 in such a manner that it faces the end of the roller conveyor 31. Moreover, a disposal chute 6 for recovering the inspection container 2 already used in the weight-determination procedure is positioned on the side of the table 1 and extends to a recovery box (not shown).

The apparatus further comprises a robot 4 which is designed in such a manner that it can move on the table 1 and the centrifugal separator 10, and towards the end of the conveying path of the roller conveyor 31 and the upper end of the disposal chute 6. The robot 4 has a linear motor automatically running along rails 4X, 4Y and 4Z, the linear motor moving towards x, y, and z directions and holding arms 4a can be opened or closed.

The inspection container 2 for accommodating a powdery resin sample may be those made of, for instance, aluminum or stainless steel. A specific example thereof is a cylinder having a sharp bottom and a fine through hole 29 as shown in FIG. 2. The inspection container 2 has a rib 33 on the upper end thereof so as to hook the holding arms 4a of the robot 4 thereon and a rib 34 in the middle and the outside of the container body 2 so as to hook the envelopes 12a, 12b, ... of the centrifugal separator 10 thereon. The through hole 29 is filled with glass wool 35 on the inside so that the plasticizer can pass therethrough while preventing any passage of the powdery resin sample therethrough. The inspection container 2 having such a sharp bottom cannot stand by itself and it is handled while accommodating it in a flat-bottomed carrier container 28 except for the centrifugation in the centrifugal separator 10. The carrier container 28 also has a rib 36 on the upper end so as to hook the holding arms 4a of the robot 4 thereon.

Figure 3:
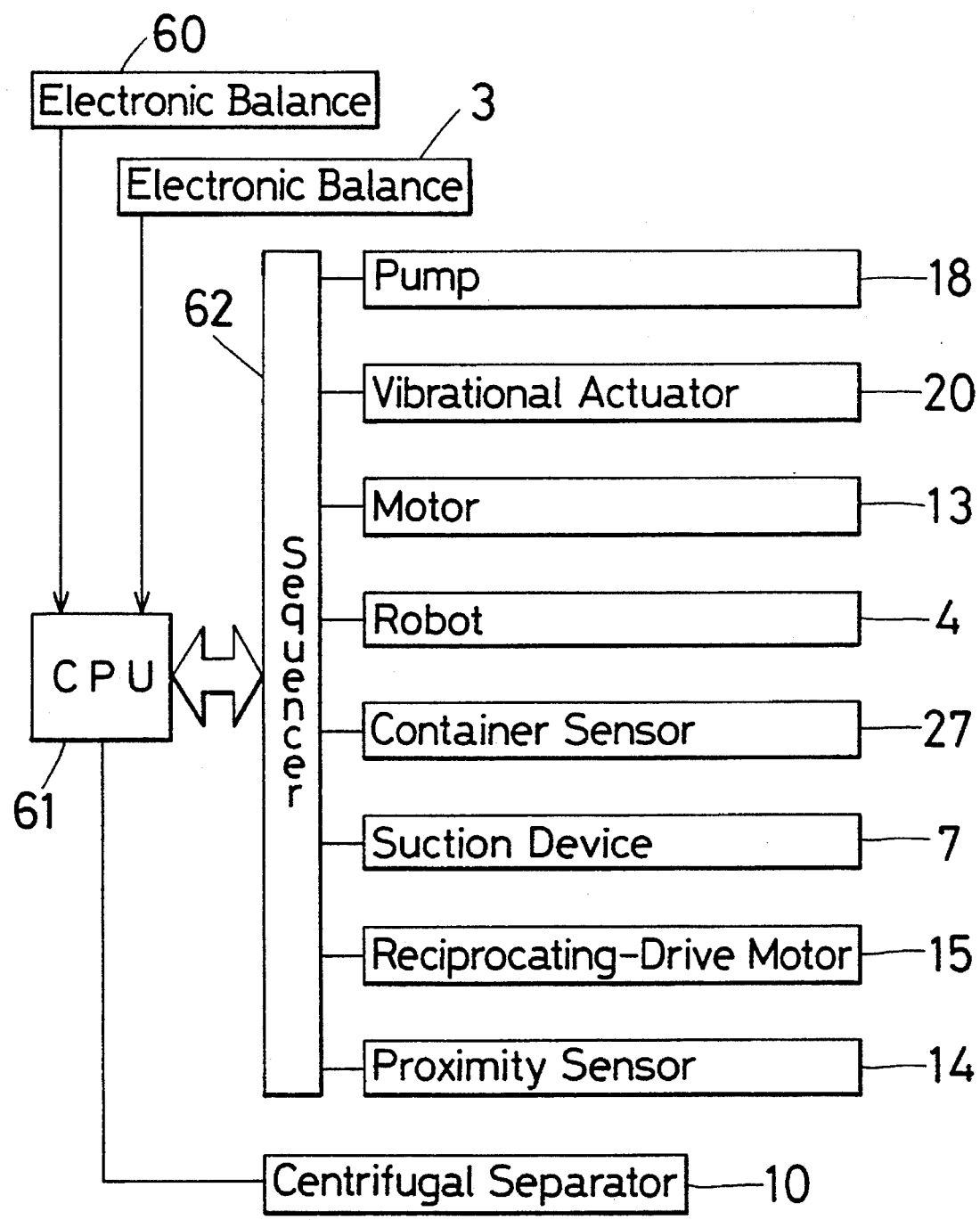
FIG. 3 is a control block diagram for use in the apparatus for automatically determining the rate of plasticizer absorption of a powdery resin according to the present invention.

In the foregoing apparatus for automatically determining the rate of plasticizer absorption of a powdery resin sample according to the present invention, as shown in FIG. 3, there are connected, to a sequencer 61, the pump 18 for the plasticizer-injection means 5, the vibrational actuator 20, the driving motor for the centrifugal separator 10, the robot 4, the container sensor 27, the suction device 7, the reciprocating-drive motor 15 for the aspiration port 9 and the proximity sensor 14 for detecting the positions of the envelopes and the sequencer 62 is in turn connected to an arithmetic unit 61 (central processing unit: CPU). The electronic balance 3 is connected to the arithmetic unit 61 and further the electronic balance 60 is likewise connected to the arithmetic unit 61.

The apparatus for automatically determining the rate of plasticizer absorption of a powdery resin sample according to the present invention is in general operated as follows.

The mechanical operations of the apparatus and the order of the operations are controlled in accordance with the control program incorporated into the sequencer 62. The measured values are calculated by the arithmetic unit 61 on the basis of the weighed values inputted from the electronic balance 3 to the arithmetic unit 61 and those inputted from the electronic balance 60 to the arithmetic unit 61. The functions of the apparatus will hereunder be explained in more detail with reference to the control program chart for the sequencer 62, shown in FIGS. 4 and 5.

A predetermined amount of a powdery resin sample is accurately weighed out by the electronic balance 60, then added to the inspection container 2 put in the carrier container 28 and the weighed value w is inputted to the arithmetic unit 61. The inspection container 2 filled with the accurately weighed out powdery resin sample and put in the carrier container 28 is mounted on the roller conveyor 31 and transferred to the subsequent step.

Figure 4:
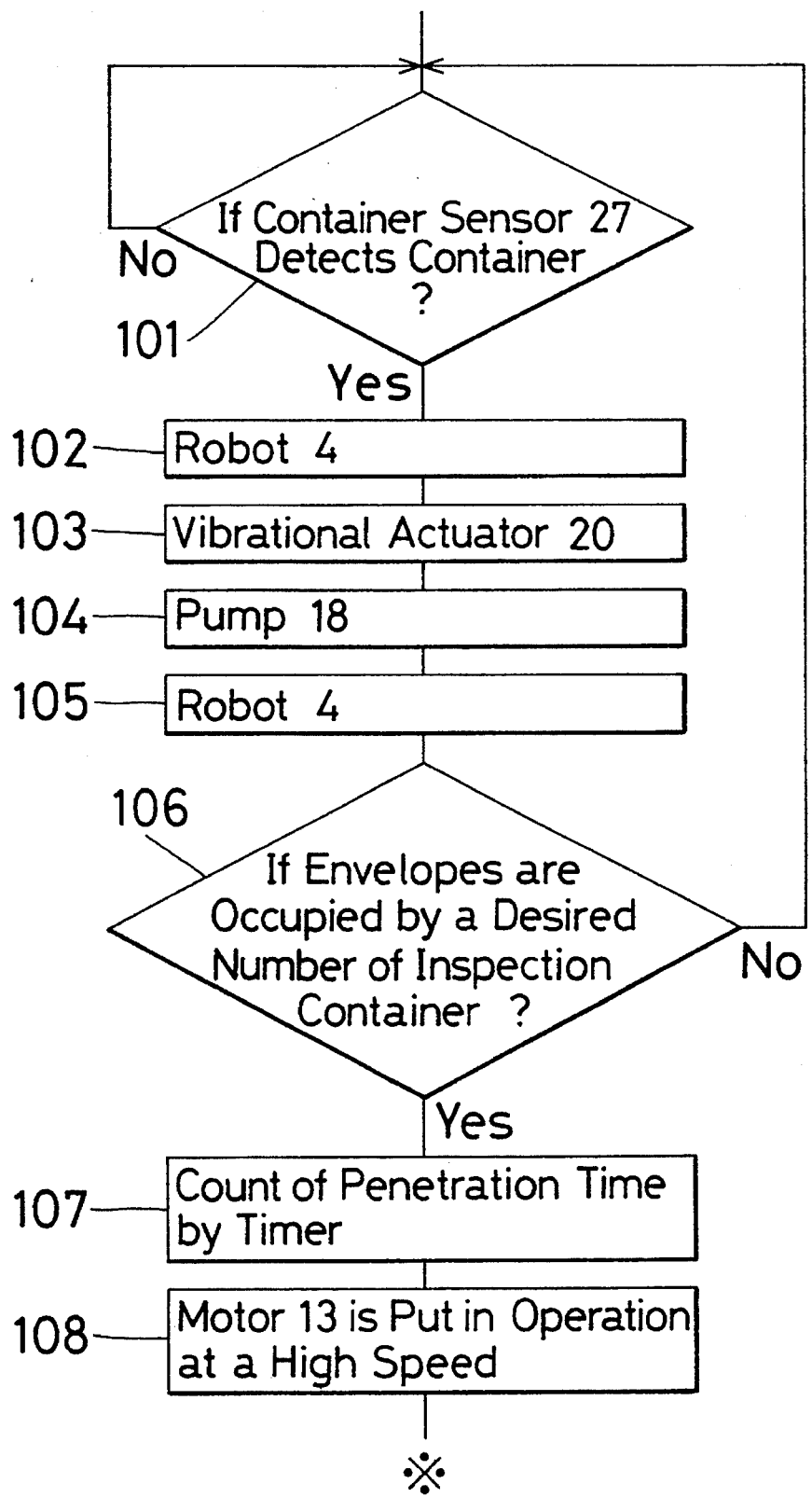
FIG. 4 is a part of the function-control program chart for use in the apparatus for automatically determining the rate of plasticizer absorption of a powdery resin according to the present invention.

In the step 101 shown in FIG. 4, if the container sensor 27 detects the presence of the inspection container 2 transferred by the roller conveyor 31, the robot 4 holds and lifts up the inspection container 2 and transfers the container 2 towards the plasticizer-injection means 5 in the step 102. At this stage, the vibrational actuator 20 is put in operation so that the plasticizer delivery tube 19 is arranged at a position just above the inspection container 2 (step 103). Then a predetermined amount of a plasticizer is introduced into the inspection container 2 by putting the pump 18 in operation (step 104). The robot 4 is again put in operation to hold the inspection container 2 and to put the container in one of the envelopes 12a, 12b, ..., for instance, the envelope 12a of the centrifugal separator 10 (step 105). After completion of this operation, it is confirmed whether all of the envelopes 12a, 12b, 12c, 12d, 12e, 12f, 12g and 12h are occupied by the inspection containers 2 in the step 106. If all of the envelopes are not occupied by the containers 2, the steps 101 to 106 are repeated over times required for the complete occupation of the envelopes. In this respect,it is also possible to forward the next step if an even number of envelopes on the diagonals are occupied by the inspection containers 2 while all of the envelopes are not occupied by the containers 2. After the predetermined envelopes are occupied by the container 2 (step 106), the time required for the penetration of the plasticizer into the powdery resin sample (about 30 minutes) is counted by a timer (step 107). Thereafter, the driving motor 13 for the centrifugal separator 10 is rotated at a high speed for a desired period of time (step 108). The excess of the plasticizer is removed from the container 2 through the glass wool layer 35 and the through hole 29 at the bottom of the inspection container 2 by the action of the centrifugal force during the rotation of the separator 10 and stored in the envelopes. Thus, only the plasticizer absorbed by and maintained in the powdery resin sample remains in the inspection container 2.

Figure 5:
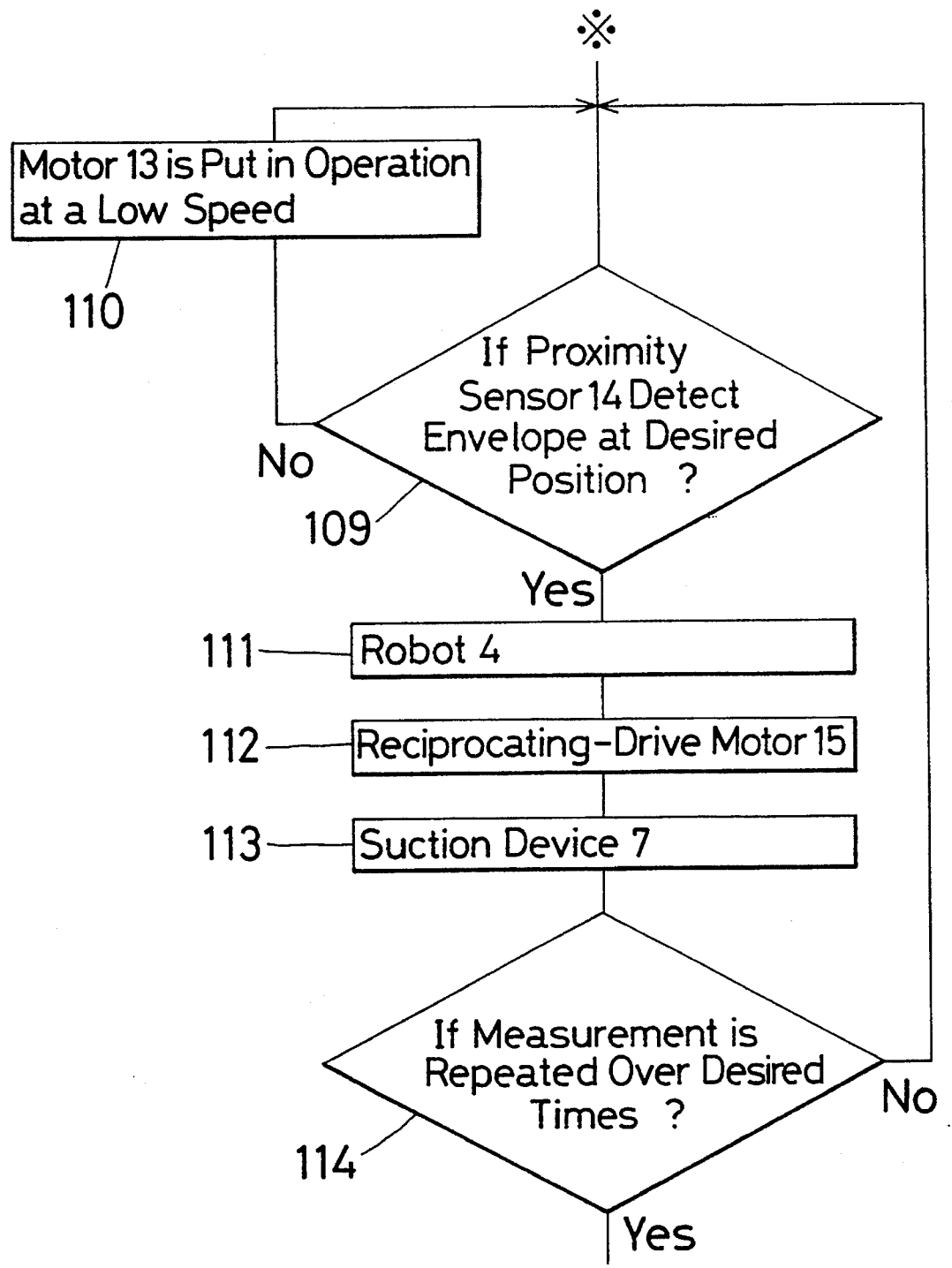
FIG. 5 is a part of the function-control program chart for use in the apparatus for automatically determining the rate of plasticizer absorption of a powdery resin according to the present invention.

After the centrifugal separator 10 is completely interrupted, it is confirmed in the step 109 shown in FIG. 5 whether the envelope 12a occupied by the inspection container 2 for the first time in the step 105 is present at a position just below the aspiration port 9 or not and if the envelope 12a is not present at the desired position, the driving motor 13 is gradually operated at a low speed till the envelope 12a reaches the desired position (step 110). Then the robot 4 is put in operation in the step 111 to hold and transfer the inspection container 2 and to put it in the carrier container 28 and further transfers the container 2 together with the carrier container 28 to the electronic balance 3 for the determination of the weight thereof. The measured weight W determined by the electronic balance 3 is inputted to the arithmetic unit 61.

On the other hand, since it is confirmed that the envelope 12a is positioned just below the aspiration port 9 in the foregoing step 109 and the inspection container 2 is pulled out from the envelope 12a in the step 111, the reciprocating-drive motor 15 is put in rotation (step 112) so that the aspiration port 9 descends and is inserted into the envelope 12a. At this stage, if the suction device 7 is put in operation (step 113), the plasticizer remaining on the bottom of the envelope 12a is aspirated into the suction device 7 through the aspiration port 9. After completion of the aspiration operation, the aspiration port 9 is ascended. In this way, a series of the steps 109 to 113 are repeated over desired times, i.e., the times corresponding to the number of the inspection containers 2 put in the envelopes 12a, 12b, 12c, 12d, 12e, 12f, 12g and 12h in this order (step 114). Thus, a series of operations of the apparatus for the determination of the rate of plasticizer absorption is completed.

At the instance when a series of the operations for determining the weight of the powdery resin sample has been completed, the weight w of the powdery resin sample per se determined by the electronic balance 60 and the weight W of the powdery resin sample containing the absorbed plasticizer determined by the electronic balance 3 are inputted to the arithmetic unit 61 in the order of the inspection containers 2 inserted into the envelopes 12a, 12b, 12c, 12d, 12e, 12f, 12g and 12h. The arithmetic unit 61 can thus calculate the rate of plasticizer absorption of each powdery resin sample according to the relation: $(W - w)/w$ in the foregoing order.

In the foregoing embodiments, dioctyl phthalate is used as a plasticizer for the determination of the rate of plasticizer absorption of a powdery resin sample, but plasticizers other than dioctyl phthalate may likewise be used in the present invention. Specific examples thereof include phthalic acid esters such as dimethyl phthalate, diethyl phthalate, diisobutyl phthalate, dibutyl phthalate, diheptyl phthalate, dinonyl phthalate, diisodecyl phthalate, ditridecyl phthalate and dicyclohexyl phthalate; phthalic acid mixed esters such as buryl benzyl phthalate, buryl lauryl phthalate and methyl oleyl phthalate; aliphatic dibasic acid esters such as diisodecyl succinate, dioctyl adipate, diisodecyl adipate, dioctyl azelate, dibutyl sebacate, dioctyl sebacate and dioctyl tetrahydrophthalate; glycol esters such as diethylene glycol dibenzoate, dipentaeythritol hexaesters and pentaerythritol esters; fatty acid esters such as buryl oleate, methyl acetylricinolate, methyl esters of chlorinated fatty acids and methyl esters of chlorinated methoxy fatty acids; and phosphoric acid esters such as tricresyl phosphate, trioctylphosphate, octyl diphenyl phosphate, triphenyl phosphate, trichloroethyl phosphate and cresyl diphenyl phosphate.

As has been explained above in detail, the apparatus for automatically determining the rate of plasticizer absorption of a powdery resin sample according to the present invention permits automatic determination of the rate of plasticizer absorption without requiring much labor. For this reason, the apparatus can provide the measured values free of any scattering depending on operators and thus can provide highly reproducible measured values. In particular, the recovery and disposal of the plasticizer generated during the removal of the excess plasticizer from the powdery resin sample can likewise be carried out automatically. This results in substantial economization of the measuring operations.

What is claimed is:

1. An apparatus for automatically determining the rate of plasticizer absorption of a powdery resin, comprising:

at least one inspection container for holding the powdery resin, said inspection container having a through hole in a bottom thereof;

an electronic balance for weighing powdery resin contained in the inspection container;

injection means for injecting plasticizer into the powdery resin contained in the inspection container;

a centrifugal separator in which the inspection container is placed, for separating and collecting non-absorbed excess plasticizer from the powdery resin;

a suction device comprising an aspiration port for aspirating the non-absorbed excess plasticizer separated and collected by the centrifugal separator;

a reciprocating-drive unit for moving the aspiration port up and down within the centrifugal separator;

a disposal chute for recovering the inspection container after determination of the rate of plasticizer absorption of the powdery resin contained therein;

robot means for transporting the inspection container, and powdery resin contained therein, to and between the electronic balance, the injection means, the centrifugal separator, and the disposal chute; and means for calculating the rate of plasticizer absorption of the powdery resin based on the weight of the powdery resin before the plasticizer is injected into the inspection container and the weight of the powdery resin after non-absorbed excess plasticizer is removed therefrom by the centrifugal separator.

2. The apparatus of claim 1, wherein the centrifugal separator further comprises a plurality of bottomed envelopes rotatable at high speed for accommodating the inspection container, wherein the non-absorbed excess plasticizer is collected in the envelopes and removed therefrom by inserting the aspiration port of the suction device into the envelopes after the inspection container is removed therefrom, and then aspirating the non-absorbed excess plasticizer through the aspiration port into the suction device.

3. The apparatus of claim 2, further comprising means for feeding, in order, the plurality of envelopes into a position at which the aspiration port moves up and down.

4. The apparatus of claim 3, wherein the means for feeding, in order, the envelopes also functions as a motor for rotating the envelopes at high speed, wherein the motor is rotated at low speed under the control of a drive-control means, and then the motor rotating at low speed is stopped at an instance when a sensor arranged at a position corresponding to that of the aspiration port detects the presence of the envelope and the aspiration port is inserted into the envelope by operating the reciprocating drive unit after the robot removes the inspection container from the envelope.

5. The apparatus of claim 1, wherein the powdery resin sample is a powdery vinyl chloride resin sample.

\* \* \* \* \*